United States Patent
Drucker

(10) Patent No.: US 7,469,434 B2
(45) Date of Patent: Dec. 30, 2008

(54) ANTI-SNORE SLEEP POSITIONING METHOD AND DEVICES

(76) Inventor: Linda W. Drucker, 1630 Arrowhead Point, Virginia Beach, VA (US) 23455

( * ) Notice: Subject to any disclaimer, the term of this patent is extended or adjusted under 35 U.S.C. 154(b) by 9 days.

(21) Appl. No.: 11/487,708

(22) Filed: Jul. 17, 2006

(65) Prior Publication Data

US 2007/0011812 A1   Jan. 18, 2007

Related U.S. Application Data

(60) Provisional application No. 60/700,025, filed on Jul. 15, 2005.

(51) Int. Cl.
*A47G 9/00* (2006.01)

(52) U.S. Cl. .................. 5/636; 5/640; 5/637

(58) Field of Classification Search ............. 5/636–637, 5/644, 630, 640, 657
See application file for complete search history.

(56) References Cited

U.S. PATENT DOCUMENTS 5,168,590 A * 12/1992 O'Sullivan ............... 5/490
5,528,784 A    6/1996 Painter
6,003,177 A * 12/1999 Ferris ....................... 5/636

FOREIGN PATENT DOCUMENTS

| DE | 91 00 663 U1 | 4/1991 |
| DE | 20 2004 012390 U1 | 9/2004 |
| EP | 0 765 647 A2 | 4/1997 |
| JP | 2000 253977 A | 9/2000 |
| JP | 2004 121816 A | 4/2004 |

* cited by examiner

*Primary Examiner*—Fredrick Conley
(74) *Attorney, Agent, or Firm*—Mendelsohn & Assoc., P.C.; Kevin M. Drucker

(57) ABSTRACT

A barrier device for sleep positioning including, in one embodiment, an elongated body to be placed atop a head-contacting surface of a pillow so as to define generally a boundary between a left side and a right side of the pillow, and at least one attachment device for securing the barrier device to the pillow. The elongated body has top and bottom ends and includes a pair of outwardly-projecting portions located at left and right sides of the elongated body near the bottom end. Each outwardly-projecting portion has an outer curvature substantially the same as and abutting at least a portion of the back of the head and/or neck of a user lying on the user's side with the user's head resting on one of the sides of the pillow.

21 Claims, 7 Drawing Sheets

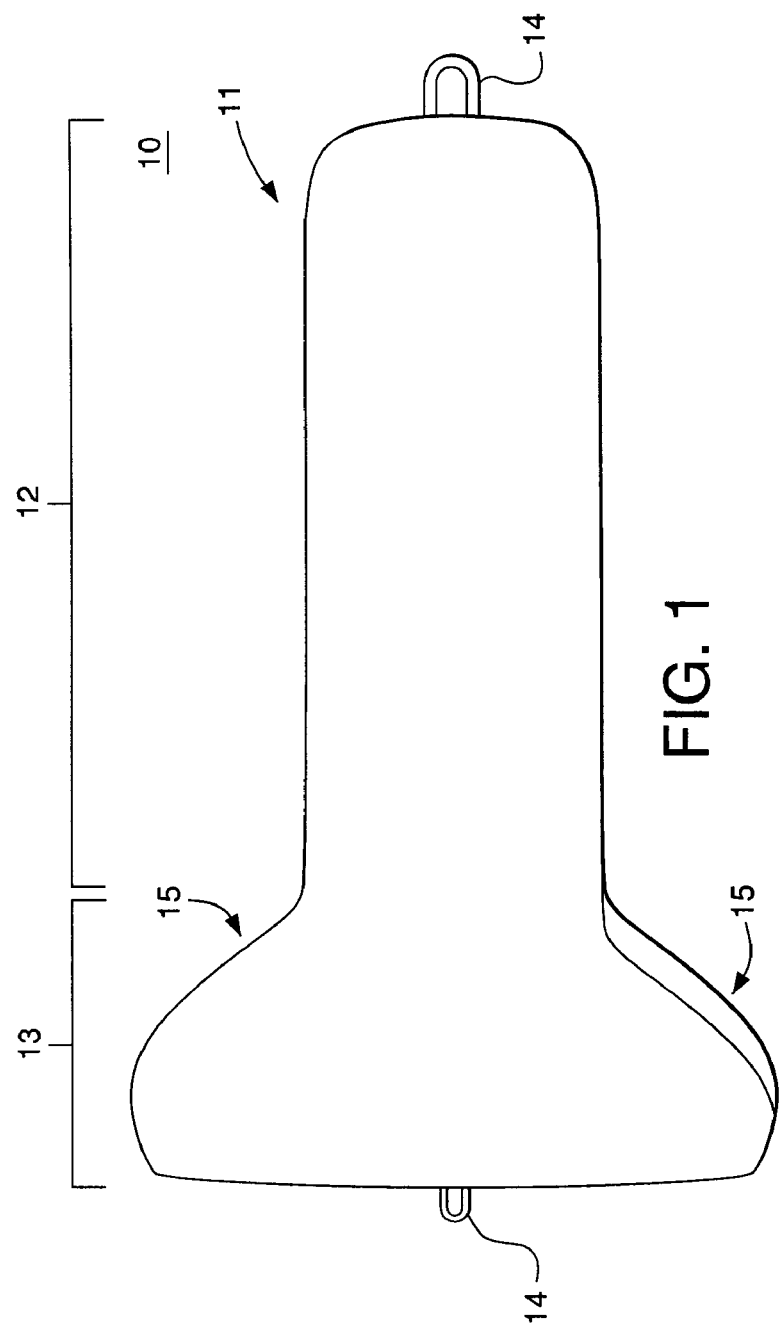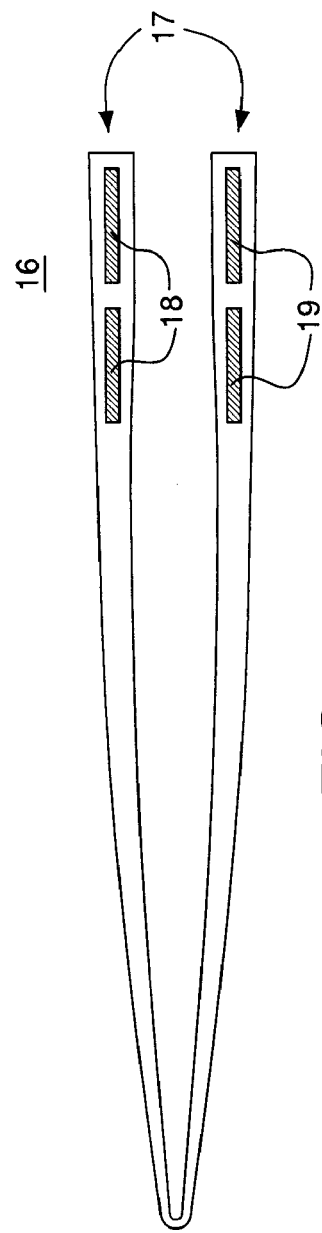
FIG. 1
FIG. 2

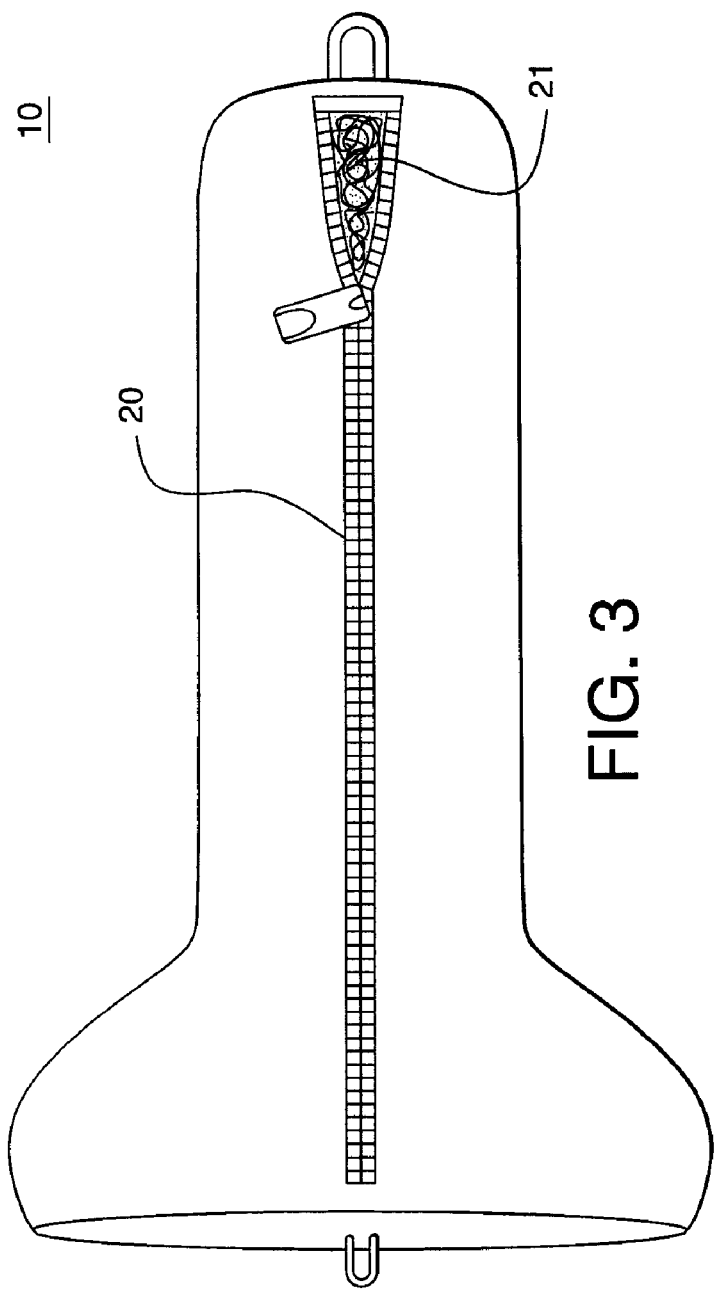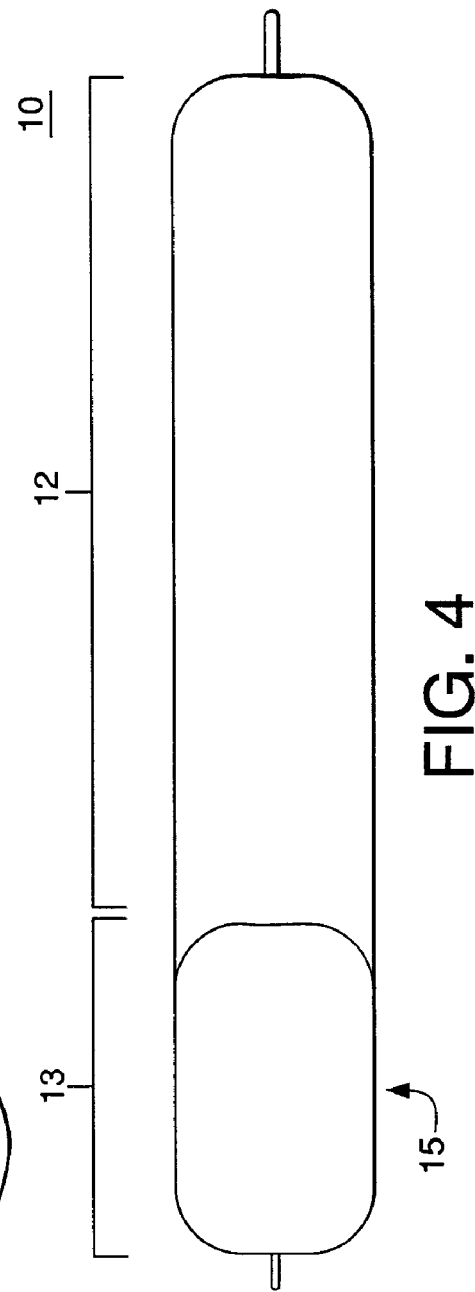

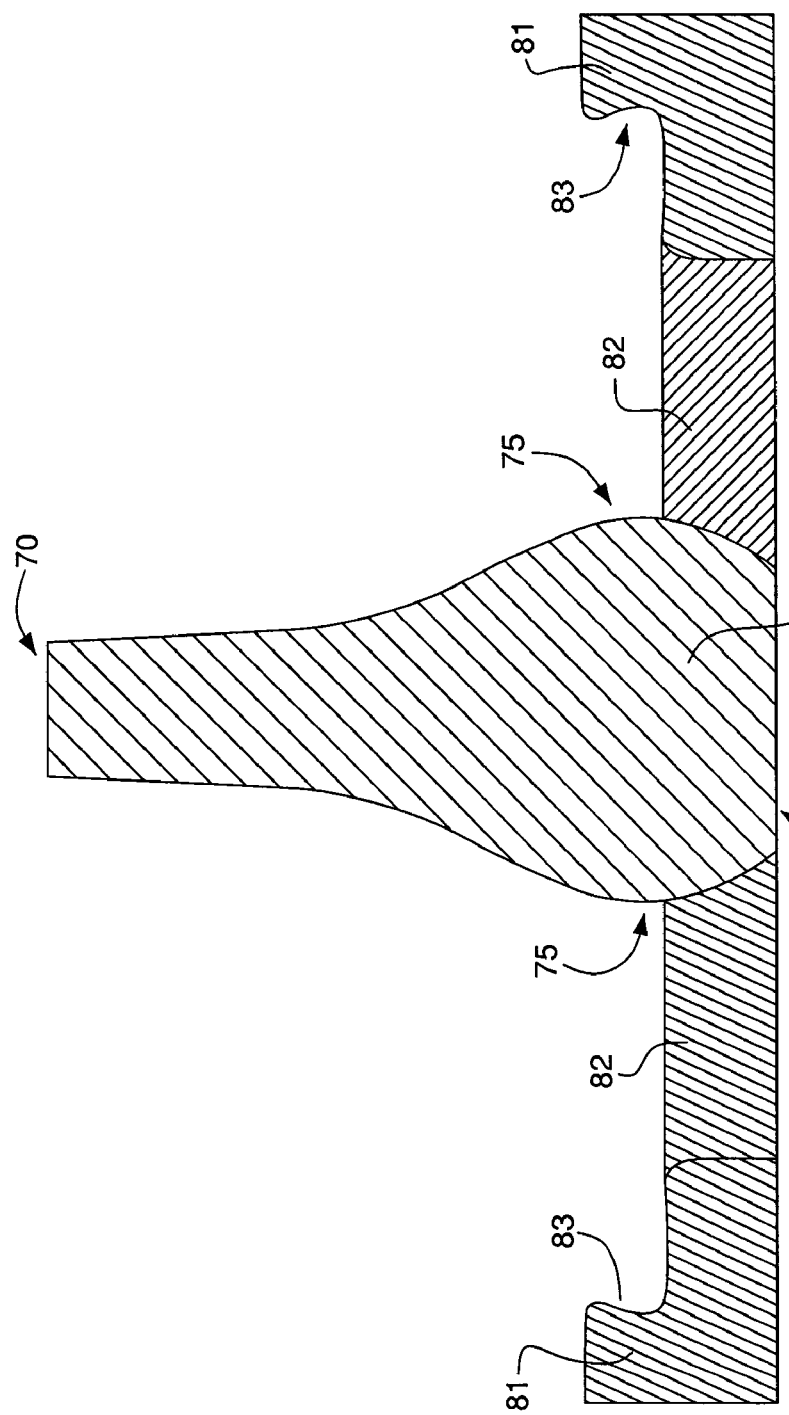

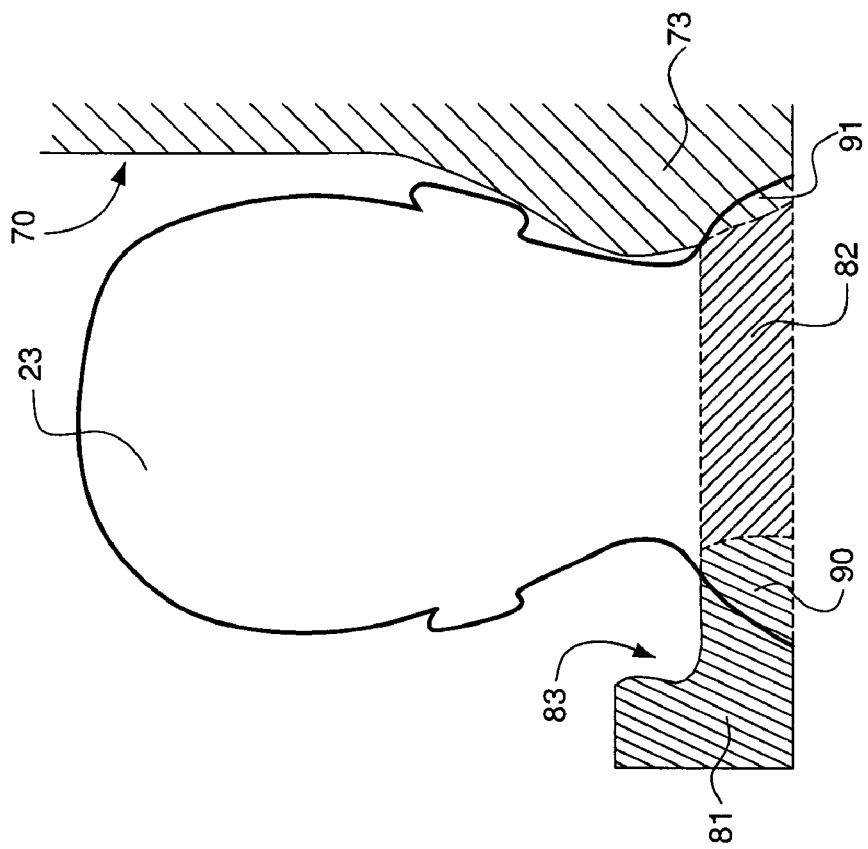
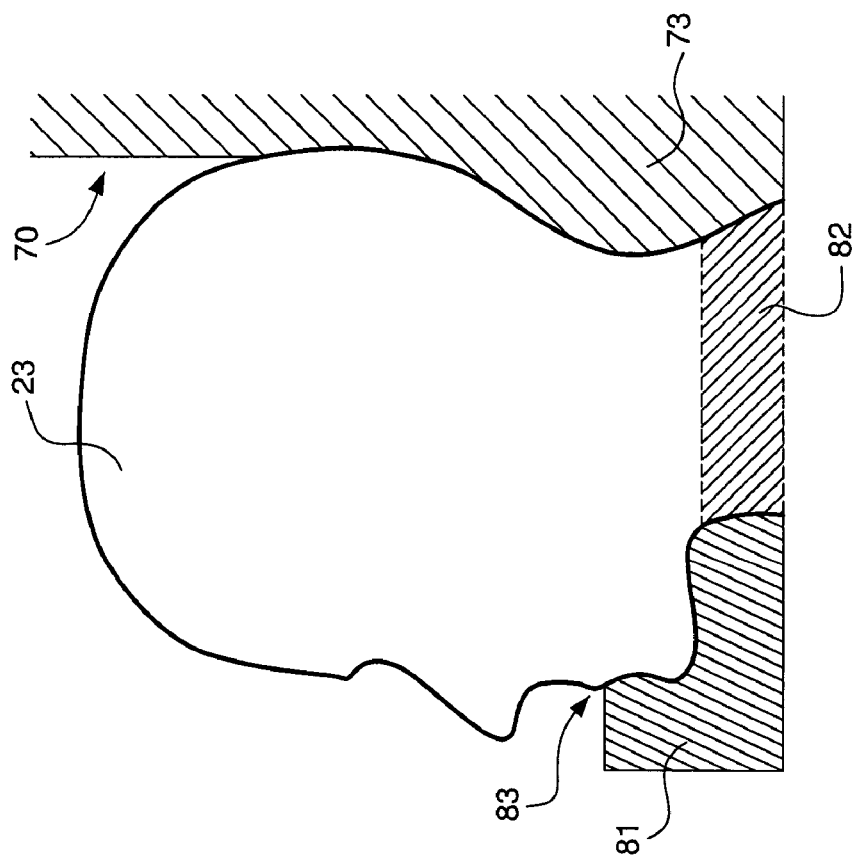

ANTI-SNORE SLEEP POSITIONING METHOD AND DEVICES

CROSS-REFERENCE TO RELATED APPLICATION

This application claims the benefit of the filing date of U.S. provisional application No. 60/700,025, filed on Jul. 15, 2005, the teachings of which are incorporated herein by reference.

BACKGROUND OF THE INVENTION

In a percentage of the population, the relaxation of muscles during sleep allows certain structures of the nose and mouth to fall backwards against the back wall of the throat. When these structures fall backwards, the airway becomes partially obstructed, and floppy excessive tissue in the upper part of the airway, e.g., the soft palate and uvula, vibrates and causes snoring. Snoring may also be due to nasal obstruction with vibration of nasal tissues or narrowing behind the tongue with vibration between the tongue and the back of the throat.

Over the years, many different (and expensive) solutions to the problem of snoring have been proposed with varying degrees of success. There are three main categories of treatment for snoring: behavior treatment, surgical treatment, and devices.

Behavior treatment includes any treatment that can be effected or administered by the snorer, such as weight loss (in people that are significantly overweight), avoiding alcohol and sleeping pills before sleep, and avoiding sleeping on the back. Avoiding sleeping on the back is most commonly attempted by fixing a tennis ball or other object to the middle of the base of the snorer's back to prevent the user from turning onto the user's back while sleeping, which can instead result in general discomfort while trying to sleep.

Surgeries and various other medical corrective procedures for snoring typically involve the removal of mouth and nose tissue. Such procedures include somnoplasty of the palate and uvula, which shrinks and stiffens the palate and uvula from inside, laser uvulopalatoplasty (LAUP), which trims off the elongated tissues, and radiofrequency ablation, which involves the use of vibration to remove tissue. These surgeries can be very expensive, extremely painful and have long recovery times with much discomfort, not to mention numerous other health risks associated with surgery. Often, tissue grows back following surgery, requiring additional surgeries or alternative corrective measures.

Devices for snore prevention include oral appliances that range from muzzle-like jaw straps that force a user's mouth to remain shut while sleeping to nightguard-type devices that cause a user's oral airway to remain forcibly obstructed by acting as an airflow barrier. Many of these devices require at least several visits to a physician or dentist and can be quite costly, typically due to being custom-fitted, such as over a user's teeth to pull the lower jaw forward while sleeping, thereby pulling the tongue away from the palate and uvula. Unfortunately, these devices can be uncomfortable and can even inflict or promote injury, including causing jaw clenching, tension headaches, and temporomandibular joint (TMJ) disorders.

Other devices include nasal passage-expanding strips, which are applied to the outside of the nose and use a strong adhesive to open the nostrils wider for quieter breathing. However, a strip-wearing snorer who rolls onto the snorer's back will still start to snore as soon as the snorer's mouth opens, and such strips can also leave sensitive skin with irritation from frequent strip application and removal.

While a number of specialized anti-snore pillows have been proposed, all have shortcomings. Many have a depression in the center to stabilize a user's head. However, this depression frequently causes the user to end up sleeping on the user's back in the center of the pillow, which promotes snoring, rather than abating it. Other specialized pillows fasten to a user's clothing or head, which not only can be uncomfortable, but can also inflict or promote injury. Moreover, having to use a specialized pillow to prevent snoring can be cumbersome while traveling, requiring a user to carry the pillow in the user's luggage or to forego using the pillow altogether until returning home.

SUMMARY OF THE INVENTION

The present invention, in certain embodiments, provides a portable and removable pillow barrier device for attachment to a user's pillow that prevents the user from turning onto the user's back while sleeping. Because the device creates resistance to the head and neck while the user is trying to turn over onto the user's back, even if the user's body starts to turn, the user will not be comfortable and will either maintain the user's present sleeping position or turn 180 degrees to sleep on the user's other side, in either case being substantially impaired from sleeping on the user's back. Accordingly, snoring caused by sleeping on one's back can be eliminated or significantly reduced.

In one embodiment, the present invention provides a barrier device for sleep positioning including an elongated body to be placed atop a head-contacting surface of a pillow so as to define generally a boundary between a left side and a right side of the pillow and at least one attachment device for securing the barrier device to the pillow. The elongated body has top and bottom ends and includes a pair of outwardly-projecting portions located at left and right sides of the elongated body near the bottom end. Each outwardly-projecting portion has an outer curvature substantially the same as and adapted to abut at least a portion of the back of the head and/or neck of a user lying on the user's side with the user's head resting on one of the sides of the pillow.

In another embodiment, the present invention provides a method of positioning a sleeping person. The method includes placing an elongated body atop a head-contacting surface of a pillow so as to define generally a boundary between a left side and a right side of the pillow. The elongated body has top and bottom ends and includes a pair of outwardly-projecting portions located at left and right sides of the elongated body near the bottom end. Each outwardly-projecting portion has an outer curvature substantially the same as and adapted to abut at least a portion of the back of the head and/or neck of a user lying on the user's side with the user's head resting on one of the sides of the pillow. The method further includes placing the user on the user's side with the head of the user atop the pillow adjacent to the elongated body, such that at least a portion of the back of the head and/or neck of the user abuts the outer curvature of one of the outwardly-projecting portions of the elongated body.

BRIEF DESCRIPTION OF THE FIGURES

FIG. 1 illustrates a top plan view of an exemplary pillow barrier device consistent with a first embodiment of the present invention;

FIG. 2 illustrates a top plan view of an exemplary strap used to secure the pillow barrier device of FIG. 1 to a pillow;

FIG. 3 illustrates a bottom plan view of the pillow barrier device of FIG. 1;

FIG. 4 illustrates a side perspective view of the pillow barrier device of FIG. 1;

FIG. 7 illustrates a top plan view of an exemplary pillow barrier device consistent with a second embodiment of the present invention;

FIG. 8 illustrates a side perspective view of the pillow barrier device of FIG. 7;

FIG. 9 illustrates an exemplary mode of using the pillow barrier device of FIG. 7;

FIG. 10 illustrates the manner in which the pillow barrier device of FIG. 7 prevents sleeping on one's back.

DETAILED DESCRIPTION

Figure 5:
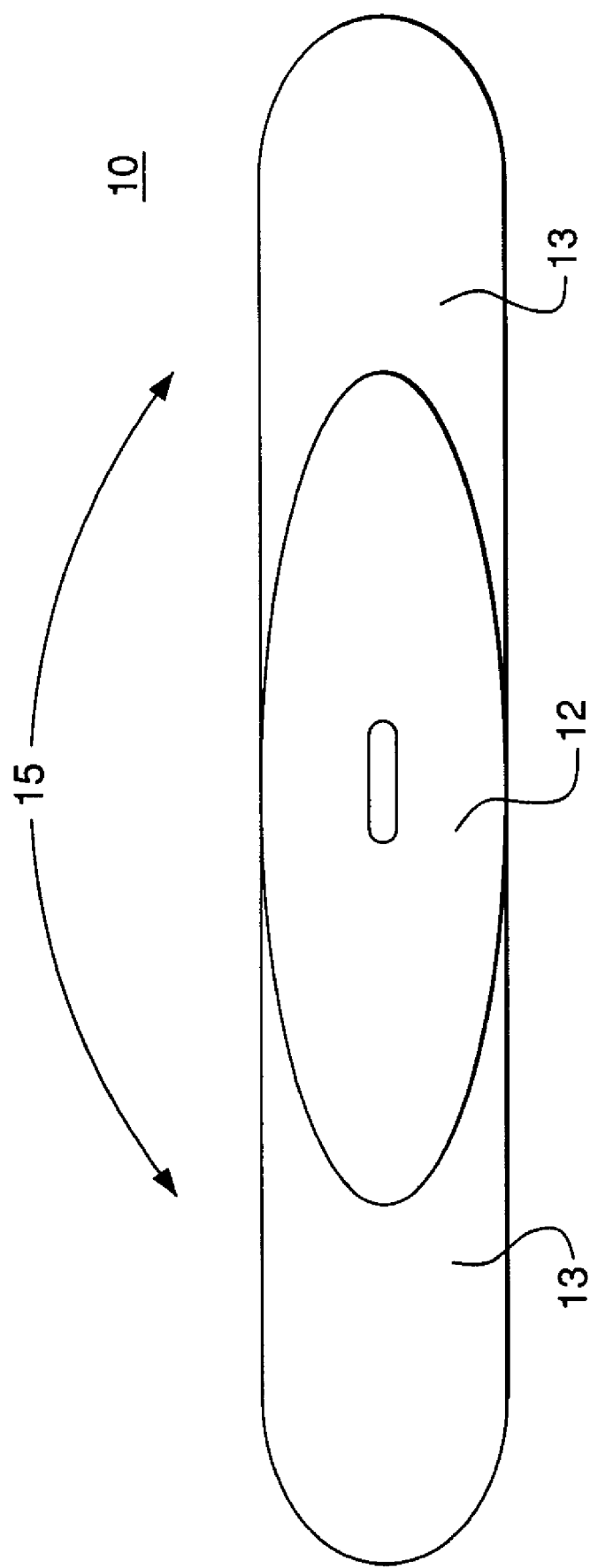
FIG. 5 illustrates an end perspective view of the pillow barrier device of FIG. 1.

The present invention provides, in one embodiment, a portable and removable pillow barrier device for placement atop an ordinary bed pillow to assist a user in remaining on the user's side while sleeping. Keeping the user on the user's side generally inhibits snoring, since the most common sleeping position that induces snoring is sleeping on one's back. The pillow barrier device functions by forming a rigid barrier that cradles the user's head and/or neck and extends from the top of the head around the back of the head and to the base of the neck. The pillow barrier device is adapted for placement on and fixation to a user's pillow along a vertical line that generally defines a boundary between the left and right sides of the top (head-facing) surface of the pillow, such that a flared (i.e., outwardly-projecting) portion of the device (i) abuts the back of the user's neck while the user sleeps on the user's side and (ii) assists in preventing the user from turning onto the user's back.

FIG. 1 illustrates a top plan view of an exemplary pillow barrier device 10 consistent with a first embodiment of the present invention. As shown in the plan view of FIG. 1, pillow barrier device 10 includes a cover 11 having an elongated body portion 12 and a base portion 13 having outer flared portions 15. Each outer flared portion 15 is contoured so as to nestle the user's head and neck, such that pillow barrier device 10 acts as an obstruction to prevent or discourage the user from turning from the user's side onto the user's back.

The overall length of cover 11 may be between 10 and 15 inches (25 to 38 cm) and is 14 inches (35 cm) in a preferred embodiment. In a preferred embodiment, the width of cover 11 at body portion 12 may be 4 inches (10 cm) and at base portion 13 may taper from 4 to 6 inches (10 to 15 cm). Cover 11 may be fabricated, e.g., from a fabric panel. The foregoing dimensions, while believed to be desirable for the use of pillow barrier device 10 with the majority of standard-sized pillows in the United States, should not be construed as limiting the dimensions of the invention in any way.

In various embodiments, the thickness (i.e., height) of pillow barrier device 10 may vary and is preferably thick enough to prevent a user's head from being able to rotate from the side-facing position (as encouraged by pillow barrier device 10) to a face-up position. Accordingly, the user should experience discomfort in attempting to rest the user's head on top of pillow barrier device 10, so that the user's body is prevented from ending up in an undesirable supine position. A loop 14 is disposed at each end of pillow barrier device 10 to facilitate fixation to a user's pillow, as will be described in further detail below.

With reference now to FIG. 2, a fabric strap 16 having two ends 17 is shown. Strap 16 is used to secure pillow barrier device 10 to a pillow. As shown in FIG. 1, sewn into (or otherwise attached to) cover 11 are a pair of loops 14, each of which is positioned to receive one end 17 of fabric strap 16 therethrough. Strap 16 is, e.g., 30 inches (76 cm) long and has two sets 18, 19 of hook-and-loop closures, one at each end, to permit strap 16 to be fastened to loops 14 of cover 11. One side of each set 18, 19 of hook-and-loop closures is, e.g., 2 inches (5 cm) long, and the other side is, e.g., 4 inches (10 cm) long, thereby permitting one set 18, 19 of hook-and-loop closures to fasten to each of loops 14, so that pillow barrier device 10 can be fastened adjustably around a pillow. Alternatively, one or more lengths of hook-and-loop fastener may be disposed along the entire underside of strap 16 to permit additional adjustability.

It should be understood that strap 16 and loops 14 are only exemplary, and that other types of straps, fastening means, and/or attachment means, e.g., an adhesive composition, may be used to secure pillow barrier device 10 to a pillow. For example, while it is contemplated that pillow barrier device 10 is installed onto a user's pillow outside of and on top of a pillowcase, in alternative embodiments, pillow barrier device 10 may be installed between the user's pillow and pillow case. In this case, a strap or other fixation mechanism might not be necessary, if pillow barrier device 10 fits snugly between the pillow and pillow case and is held substantially in place by friction, although straps or other fixation mechanisms may still be used.

FIG. 3 illustrates a bottom plan view of pillow barrier device 10 with a zipper 20 disposed along body portion 12. As shown, pillow barrier device 10 is filled with batting 21 to provide rigidity, and zipper 20 (shown partially unzipped) retains batting 21 within cover 11. Zipper 20 may be an "invisible" type, to reduce the incidence of user discomfort from contact with the zipper during use. Zipper 20 permits access to batting 21, e.g., to clean or wash cover 11, or to remove or replace batting 21. Accordingly, an additional pouch or coverlet (not shown) may be provided between batting 21 and cover 11 to permit batting 21 to retain its shape while separated from cover 21, thereby facilitating reinsertion of batting 21 into cover 11 after washing or cleaning. One or more gussets or expansion seams may be disposed within pillow barrier device 10 to aid in proper distribution of batting or other filler materials.

It should be recognized that one or more filler materials other than batting may be used, e.g., cotton, polyester, polystyrene, a single piece of polyurethane foam or memory foam sized and shaped to fill and provide support to cover 11, or a lightweight, closed-cell polyethylene foam (as used, e.g., to construct swimming pool "noodle" toys), etc. An elongated I-shaped or T-shaped "spine" (or core) along the length of pillow barrier device 10 may be constructed from one or more rigid materials (e.g., polyurethane or polyethylene foam) and may be disposed centrally within the device, with less rigid material (e.g., cotton batting) surrounding the spine to maintain the spine securely in place centrally within the device.

One or more sealable bladders or compartments may be provided instead of, or in addition to, batting or other filler materials or a spine. Such bladders or compartments may be filled with air (e.g., using an integrated apparatus for inflation/deflation for adjustability), water, or another fluid to add rigidity to pillow barrier device 10. Alternatively or additionally, pillow barrier device 10 may be filled with a heat-retentive or cold-retentive composition, e.g., buckwheat hulls, rice, corn, corn husks, water, ice, a specialized gel, or other materials, to permit cold or heat therapy to be applied to the neck and/or head of a user of pillow barrier device 10.

It should also be recognized that a fastener other than a zipper, e.g., hook-and-loop fastener, snaps, buttons, adhesive, etc. may be used to open and close cover 11, and that one or more openings to access the batting, filling, or core may be located anywhere on cover 11 to permit removal or replacement of the batting, filling, or core, or to permit washing of cover 11.

FIG. 4 illustrates a side perspective view of pillow barrier device 10, and FIG. 5 illustrates an end perspective view of pillow barrier device 10. As shown, body portion 12 has a substantially elliptical cross-section, and base portion 13 is generally of the same thickness as body portion 12 (although, in alternative embodiments, it is contemplated that the thickness of base portion 13 could reduce gradually as base portion 13 tapers toward outer flared portions 15, to provide a more gradual slope to support the user's head and neck).

Figure 6:
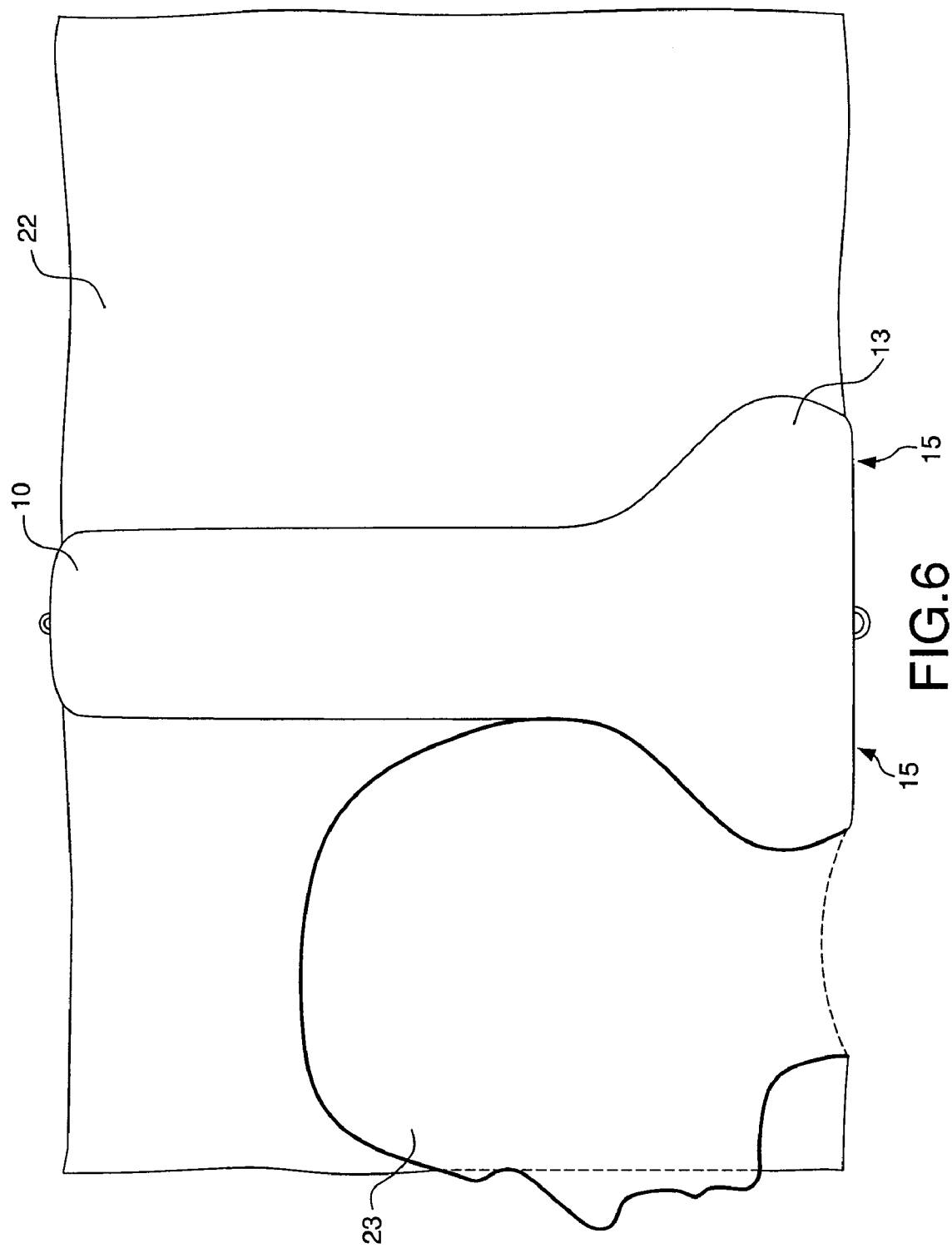
FIG. 6 illustrates an exemplary mode of using the pillow barrier device of FIG. 1.

FIG. 6 illustrates an exemplary mode of using pillow barrier device 10, wherein, to demonstrate user positioning, the outline of the head and neck of a side-resting user 23 is superimposed on a pillow 22 on which pillow barrier device 10 is installed. As shown, user 23 has placed pillow barrier device 10 vertically at the center of the pillow 22, such that base portion 13 is disposed along the portion of the top (head-facing) surface of pillow 22 closest to the neck of user 23. User 23 has already brought strap 16 (not shown in FIG. 6) around the underside of pillow 22 and threaded the ends 17 of strap 16 through loops 14, pulling the ends taut to secure pillow barrier device 10 to pillow 22. As shown, user 23 places the user's head on either the left side (facing left) or the right side (facing right) of pillow 22, so that user 23 can feel one of outer flared portions 15 abut the back of the user's neck and/or head. If user 23 attempts to change sides, whether asleep or awake, one of the following two results should occur: (i) user 23 is prevented from turning onto the user's back by the inability to rotate the user's head toward the center of pillow 22 due to the position of pillow barrier device 10, such that the user continues sleeping on the user's same side; or (ii) user 23 is permitted to rotate the user's body by approximately 180 degrees by rolling or lifting the user's head onto and then past pillow barrier device 10, resulting in a 180-degree turn of the user's head and body, such that the user continues sleeping on the user's opposite side. Thus, while pillow barrier device 10 is in place, snoring can be inhibited by preventing user 23 from sleeping on the user's back.

While pillow barrier device 10 may be used with pillows having a variety of shapes and sizes, it is desirable that the pillow be sized so that user 23 does not have any room to sleep on the user's back adjacent to pillow barrier device 10 while pillow barrier device 10 is in place. Thus, as shown in FIG. 6, when pillow barrier device 10 is used with an optimally-sized pillow such as pillow 22, the head of user 23 may overhang the end of pillow 22 while pillow barrier device 10 is in place, such that there would be no room for the head of the user 23 to rest face-up on pillow 22 to the left or right of pillow barrier device 10.

FIG. 7 illustrates in top plan view, and FIG. 8 illustrates in side perspective view an exemplary pillow barrier device 70 consistent with a second embodiment of the invention. Device 70 is substantially similar to device 10, except that (i) device 70 tapers not only outwardly but also inwardly at its flared portions 75 toward bottom end 71 of base portion 73, and (ii) device 70 includes a pair of chin supports 81 coupled to base portion 73 via a pair of connector portions 82. Device 70, including chin supports 81, may be constructed of the same or similar materials as device 10 and may or may not include a removable cover (not shown). On both the left and right sides of device 70, the inward tapering at flared portion 75 conforms substantially to the curvature of the back of the neck of a user positioned with the user's neck resting against flared portion 75. On both the left and right sides of device 70, chin support 81 has substantially the same thickness as base portion 73 and has a chin-facing portion 83 having a curvature conforming substantially to the chin of a user positioned with the user's neck resting against flared portion 75 and the user's chin resting against chin support 81. Connector portions 82 have a relatively small thickness and serve to keep chin supports 81 in place at a given distance relative to base portion 73. This distance can be made adjustable to suit users having variously-sized necks, e.g., by using hook-and-loop fastener disposed on base portion 73 and connector portions 82 to couple connector portions 82 at various distances from base portion 73.

FIG. 9 illustrates an exemplary mode of using pillow barrier device 70, wherein, to demonstrate user positioning, the outline of the head and neck of a side-resting user 23 is superimposed over pillow barrier device 70. The mode of using pillow barrier device 70 is substantially similar to the mode of using pillow barrier device 10 (as shown in FIG. 6), with the addition of the chin of the user resting against the chin-shaped curvature of chin-facing portion 83 of chin support 81. With the distance between chin support 81 and base portion 73 properly adjusted to fit the neck of user 23, the neck of user 23 is disposed directly above connector portion 82, and chin support 81 and base portion 73 abut the user's head, assisting the user's head in maintaining a side-facing position. FIG. 10 illustrates a situation in which a user might attempt to rotate onto the user's back while using pillow barrier device 70. To demonstrate the resulting uncomfortable or practically unfeasible user positioning in this scenario, the outline of the head and neck of a supine user 23 is superimposed over pillow barrier device 70. As shown in FIG. 10, if user 23 attempts to rotate onto the user's back, there is no clearance to permit the user's head to rest anywhere between area 90 of chin support 81 and area 91 of base portion 73, and the user is thereby prevented from rotating onto the user's back. The user is, however, permitted to rotate the user's body by approximately 180 degrees by rolling or lifting the user's head onto and then past pillow barrier device 70, resulting in a 180-degree turn of the user's head and body, such that the user continues sleeping on the user's opposite side. Thus, while pillow barrier device 70 is in place, snoring can be inhibited by preventing user 23 from sleeping on the user's back.

Figure 11:
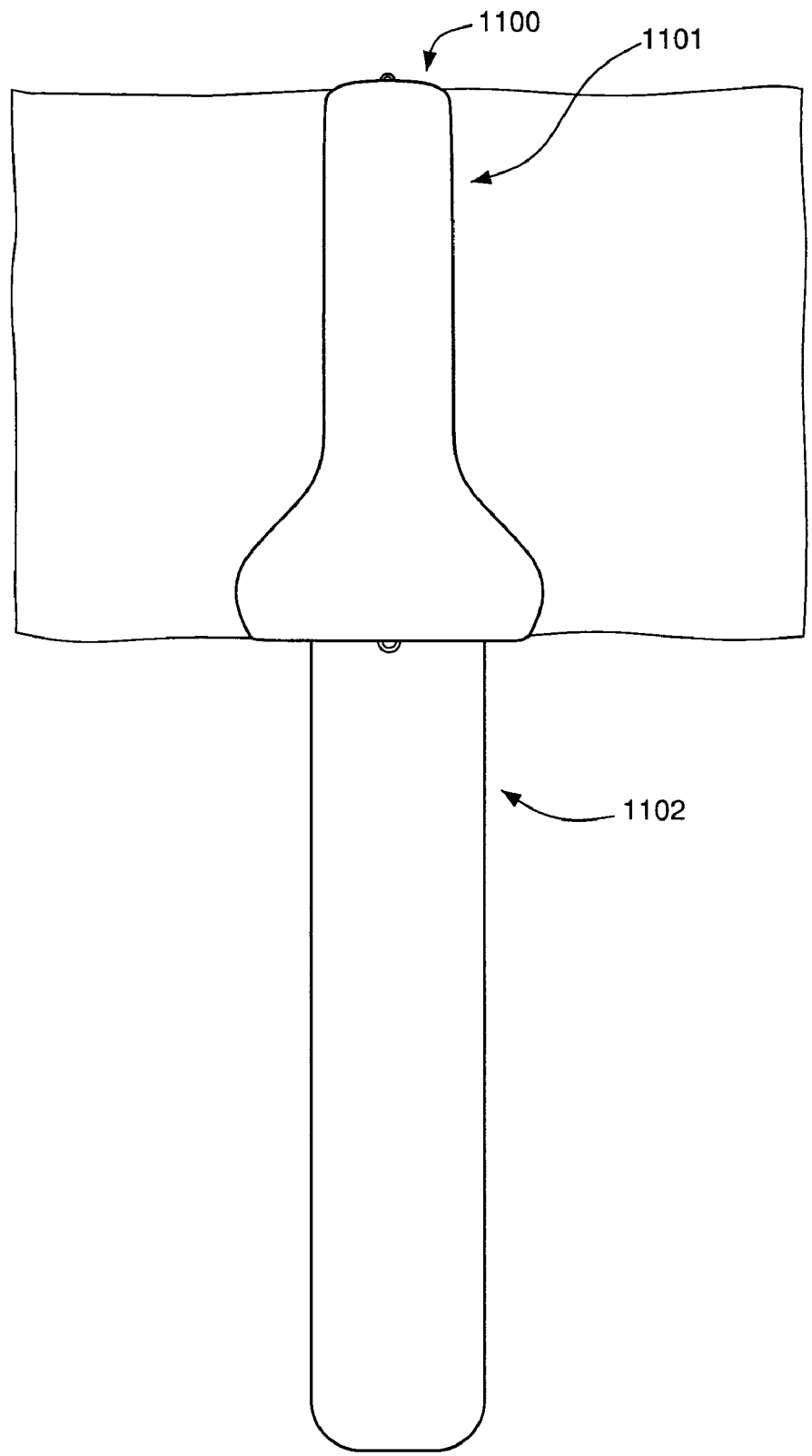
FIG. 11 illustrates a top plan view of an exemplary pillow barrier device consistent with a third embodiment of the present invention.

FIG. 11 illustrates an exemplary pillow barrier device 1100 consistent with a third embodiment of the present invention, depicted in an exemplary installation on a user's pillow. In this embodiment, device 1100 includes head-contacting portion 1101 and extension portion 1102, which projects downward from head-contacting portion 1101 in a direction substantially parallel to the user's body. Device 1100, including extension portion 1102, may be constructed of the same or similar materials as device 10 and may or may not include a removable cover (not shown). Extension portion 1102, in various embodiments, may be of varying shapes, lengths, thicknesses, and other dimensions and may connect to head-contacting portion 1101 using, e.g., hook-and-loop fastener. Extension portion 1102 extends the functionality of head-contacting portion 1101 by serving as an additional barrier, to prevent the user's body from ending up in a supine position.

Accordingly, during use, the user's back abuts extension portion 1102 while the user is in a side-facing position with the user's head abutting either the left side or the right side of head-contacting portion 1101.

The above-described modes of operation assume that the pillow barrier device is used continuously and repeatedly during sleep periods to prevent snoring. However, it should also be recognized that, in other exemplary modes of operation, a pillow barrier device consistent with various embodiment of the present invention can be used as a training device to teach a user to sleep on the user's side, rather than on the user's back. Accordingly, a user who has become trained to sleep only on the user's side by continuously and/or repeatedly using the pillow barrier device may be able to cease using the pillow barrier device after a certain period of time, with the benefit of continued inhibition of snoring long after the now-trained user's use of the pillow barrier device ceases.

While the present invention is described above as having utility in the cessation of snoring, other uses may be possible, such as in treating sleep apnea (possibly in conjunction with other medical treatments, such as an oral airway dilator or continuous positive airway pressure (CPAP) device), preventing the aggravation of existing bodily injuries, or other scenarios in which sleeping on one's back is undesirable and/or sleeping on one's side is desirable.

It should be understood that the phrase "pillow barrier device," as used herein, should not be construed as limiting the invention to devices used with pillows, and it is contemplated that devices consistent with various embodiments of the present invention may be used without pillows and/or with cushions or other bedding-related devices. Furthermore, the term "pillow" should be broadly construed as defining a pillow either with or without a pillowcase, cover, sham, or other covering.

While, in the embodiments depicted and described herein, embodiments of pillow barrier devices consistent with the present invention include flared portions having certain shapes and dimensions, in alternative embodiments, the flared portions may be dimensioned and shaped in ways other than as depicted and described herein, and, in certain embodiments, it is possible that flared portions could be eliminated altogether. In embodiments that include flared portions, each of the flared portions desirably has an outer curvature that is substantially the same as at least a portion of the back of the head and/or neck of a user lying on the user's side, with the back of the user's head and/or neck abutting the outer curvature.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

A device consistent with the present invention may also be used in conjunction with other anti-snoring devices (e.g., nostril-expanding adhesive strips), sleep-positioning devices (e.g., knee-rest pillows), and bedding devices (e.g., memory-foam pillows and/or mattresses), to provide enhanced comfort and/or enhanced relief from snoring.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Unless explicitly stated otherwise, each numerical value and range should be interpreted as being approximate as if the word "about" or "approximately" preceded the value of the value or range.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

It should be appreciated that embodiments of the invention described herein are merely exemplary, and that the present invention may be embodied in structural and/or functional components other than those specifically set forth herein, without departing from the present invention. Thus, the present invention is intended to cover all such alternatives, modifications, and equivalents as may be included within the spirit and broad scope of the invention, as expressed in the following claims.

I claim:

1. A barrier device for sleep positioning comprising:
    an elongated body adapted for placement atop a head-contacting surface of a pillow so as to divide the head-contacting surface of the pillow into a left sleeping surface and a right sleeping surface, with the elongated body serving as a barrier between the left and right sleeping surfaces to inhibit a user from sleeping on top of the elongated body and promote sleeping on either the left or right sleeping surface; and
    at least one attachment device for securing the barrier device to the pillow,
    wherein:
        the elongated body has top and bottom ends and comprises a pair of outwardly-projecting portions located at left and right sides of the elongated body near the bottom end; and
        each outwardly-projecting portion has an outer curvature substantially the same as and adapted to abut at least a portion of the back of the head and/or the back of the neck of a user lying on the user's side with the user's head resting on either the left or right sleeping surface.

2. The invention of claim 1, wherein the elongated body is substantially resilient.

3. The invention of claim 1, wherein the barrier device is adapted to be secured to the pillow by placement of the barrier device between the pillow and a pillowcase covering the pillow.

4. The invention of claim 1, wherein the barrier device further comprises a cover at least partially filled with one or more filler materials.

5. The invention of claim 1, wherein at least a portion of the elongated body is substantially rigid.

6. The invention of claim 1, wherein the barrier device further comprises a sealable bladder adapted to retain one or more fluids to add rigidity to the barrier device.

7. The invention of claim 1, wherein the barrier device further comprises one or more heat-retentive or cold-retentive materials.

8. The invention of claim 1, wherein the barrier device further comprises a pair of chin supports coupled to the elongated body.

9. The invention of claim 8, wherein each chin support has a chin-facing portion having a curvature conforming substantially to the chin of the user lying on the user's side with the user's head resting on either the left or right sleeping surface and abutting the outer curvature of the outwardly-projecting portion of the elongated body.

10. The invention of claim 1, further comprising an elongated extension portion coupled to the elongated body and extending from the bottom end of the elongated body in a direction substantially parallel to the body of the user, wherein the elongated extension portion extends so as to abut at least a portion of the back of the user lying on the user's side with the user's head resting on either the left or right sleeping surface.

11. A method of positioning a sleeping person, the method comprising:
   (a) placing an elongated body atop a head-contacting surface of a pillow so as to divide the head-contacting surface of the pillow into a left sleeping surface and a right sleeping surface, with the elongated body serving as a barrier between the left and right sleeping surfaces to inhibit a user from sleeping on top of the elongated body and promote sleeping on either the left or right sleeping surface, wherein:
   the elongated body has top and bottom ends and comprises a pair of outwardly-projecting portions located at left and right sides of the elongated body near the bottom end; and
   each outwardly-projecting portion has an outer curvature substantially the same as and adapted to abut at least a portion of the back of the head and/or the back of the neck of a user lying on the user's side with the user's head resting on either the left or right sleeping surface; and
   (b) positioning the user on the user's side with the head of the user atop either the left or right sleeping surface adjacent to the elongated body, such that at least a portion of the back of the head and/or the back of the neck of the user abuts the outer curvature of one of the outwardly-projecting portions of the elongated body.

12. The invention of claim 11, further comprising securing the elongated body to the pillow using at least one attachment device.

13. The invention of claim 11, further comprising securing the elongated body to the pillow by placement of the elongated body between the pillow and a pillowcase covering the pillow.

14. The invention of claim 11, wherein the elongated body further comprises a cover at least partially filled with one or more filler materials.

15. The invention of claim 11, wherein the elongated body further comprises a substantially rigid spine disposed along at least a portion of the elongated body.

16. The invention of claim 11, wherein the elongated body further comprises a sealable bladder adapted to retain one or more fluids to add rigidity to the baffler device.

17. The invention of claim 11, wherein the elongated body further comprises one or more heat-retentive or cold-retentive materials disposed on or in the elongated body.

18. The invention of claim 11, wherein the elongated body further comprises a pair of chin supports coupled to the elongated body.

19. The invention of claim 18, wherein each chin support has a chin-facing portion having a curvature conforming substantially to the chin of the user lying on the user's side with the user's head resting on either the left or right sleeping surface and abutting the outer curvature of the outwardly-projecting portion of the elongated body.

20. The invention of claim 11, wherein the elongated body further comprises an elongated extension portion coupled to the elongated body and extending from the bottom end of the elongated body in a direction substantially parallel to the body of the user, wherein the elongated extension portion extends so as to abut at least a portion of the back of the user lying on the user's side with the user's head resting on either the left or right sleeping surface.

21. The invention of claim 11, wherein the elongated body is substantially resilient.

* * * * *